(12) United States Patent
Li et al.

(10) Patent No.: US 10,483,628 B2
(45) Date of Patent: Nov. 19, 2019

(54) ANTENNA AND ATTACHMENT METHOD FOR RECHARGEABLE IMPLANTABLE MEDICAL DEVICE

(71) Applicant: PACESETTER, INC., Sylmar, CA (US)

(72) Inventors: Perry Li, Arcadia, CA (US); James T. Dean, McKinney, TX (US); Christopher A. Crawford, Carrollton, TX (US)

(73) Assignee: Pacesetter, Inc., Sylmar, CA (US)

( * ) Notice: Subject to any disclaimer, the term of this patent is extended or adjusted under 35 U.S.C. 154(b) by 421 days.

(21) Appl. No.: 15/345,187

(22) Filed: Nov. 7, 2016

(65) Prior Publication Data

US 2017/0179579 A1 Jun. 22, 2017

Related U.S. Application Data

(60) Provisional application No. 62/268,981, filed on Dec. 17, 2015.

(51) Int. Cl.
| | |
|---|---|
| *H01Q 1/12* | (2006.01) |
| *H01Q 1/27* | (2006.01) |
| *H01Q 13/08* | (2006.01) |
| *H04B 5/00* | (2006.01) |
| *A61N 1/00* | (2006.01) |
| *A61B 5/00* | (2006.01) |
| *A61N 1/372* | (2006.01) |
| *G06K 19/077* | (2006.01) |

(52) U.S. Cl.
CPC ............. *H01Q 1/273* (2013.01); *H01Q 13/08* (2013.01); *H04B 5/00* (2013.01); *H04B 5/0031* (2013.01); *H04B 5/0037* (2013.01); *A61B 5/0031* (2013.01); *A61N 1/37229* (2013.01); *G06K 19/07758* (2013.01)

(58) Field of Classification Search
CPC ............. H01Q 1/273; G06K 19/07758; A61B 5/0031; A61N 1/37229; A61N 1/37254; A61N 1/375; A61N 1/37512; A61N 1/37516; A61N 1/37518; A61N 1/3754; A61N 1/3756; A61N 1/3752; Y10S 128/903
USPC ......... 343/718, 873; 29/600; 607/32, 36, 37, 607/57, 60, 156
See application file for complete search history.

(56) References Cited

U.S. PATENT DOCUMENTS

| | | | |
|---|---|---|---|
| 8,972,021 B2 * | 3/2015 | Edgell et al. ...... | A61N 1/37229 607/60 |
| 2011/0190833 A1 * | 8/2011 | Ries et al. ............. | A61N 1/375 607/2 |

* cited by examiner

*Primary Examiner* — Binh B Tran (57) ABSTRACT

Devices and methods are provided for an implantable medical device (IMD) comprising a device housing having electronic components therein, a feedthrough assembly joined to the device housing, an antenna assembly, and a header body mounted to the device housing and enclosing the antenna assembly and feedthrough assembly. The antenna assembly including an inner conductor, a dielectric material, and an outer conductor arranged to form a coaxial structure.

18 Claims, 9 Drawing Sheets

ANTENNA AND ATTACHMENT METHOD FOR RECHARGEABLE IMPLANTABLE MEDICAL DEVICE

CROSS REFERENCE TO RELATED APPLICATIONS

This application claims the benefit of U.S. Provisional Application Ser. No. 62/268,981, filed Dec. 17, 2015.

BACKGROUND OF THE INVENTION

Embodiments of the present disclosure generally relate to implantable medical devices, and more particularly to antenna and attachment mechanisms for use with rechargeable implantable medical devices.

An implantable medical device (IMD) is a medical device that is implanted in a patient to, among other things, monitor electrical activity of a heart, and optionally to deliver therapy. An IMD may record cardiac activity of a patient over time and report such cardiac activity to an external device. The IMD device may optionally perform various levels of sophisticated analysis of the cardiac activity and based thereon perform additional recording operations. The IMD may also be configured to deliver appropriate electrical and/or drug therapy. Examples of IMDs include cardiac monitoring devices, pacemakers, cardioverters, cardiac rhythm management devices, defibrillators, neurostimulators and the like. The electrical therapy produced by an IMD may include, for example, pacing pulses, cardioverting pulses, and/or defibrillator pulses. The device is used to both provide treatment for the patient and to inform the patient and medical personnel of the physiologic condition of the patient and the status of the treatment.

In general, an IMD includes a battery, memory and electronic circuitry that are hermetically sealed within a metal housing (generally referred to as the "can"). The metal housing typically is formed of titanium and includes a shell with an interconnect cavity, in which the memory, pulse generator and/or processor module reside. The device housing is configured to receive a header assembly. The header assembly comprises a mechanical structure which houses an antenna and a sensing electrode. A feedthrough assembly is located at a header receptacle area and is sealed to the device housing to form an interface for conductors to enter/exit the interconnect cavity.

Some IMDs communicate with external devices and/or other implanted devices through an RF antenna. One of the primary requirements for an RF antenna operating within an implantable medical device is to fit within the small size of a device header while maintaining a satisfactory level of RF performance. Conventional IMDs include an antenna that coexists with other metallic structures in the header such as leads and connector blocks.

However, recent developments with rechargeable IMDs have presented an additional challenge. In at least one proposed rechargeable IMD, a charge coil is provided in the device header where the charge coil comes into close proximity with the antenna. The charge coil both restricts the size of the antenna and creates a potential RF coupling effect with the antenna. The coupling effect causes RF energy to leak out of the antenna to the coil where the RF energy is lost. The coupling effect decreases the signal power exhibited by the antenna thereby degrading RF performance.

Conventional antennas utilize antenna configurations that do not fit within the tight space requirements of a rechargeable IMD when the charge coil in the header. Further, conventional IMD antenna, such as the monopole or loop antennas, suffer undue degradation due to RF coupling when the charge coil is added to the header.

A need remains for a new type of antenna that is both small and does not experience undue performance degradation in the presence of nearby metal objects like a charge coil.

Further, conventional attachment mechanisms that couple the antenna to a feedthrough experience certain limitations. In particular, conventional attachment mechanisms complicate the assembly and manufacturing process.

A need remains for an improved attachment mechanism between the feedthrough assembly and electronic components within the device header.

SUMMARY

In accordance with embodiments herein, an implantable medical device (IMD) is provided comprising a device housing having electronic components therein, a feedthrough assembly joined to the device housing, an antenna assembly, and a header body mounted to the device housing and enclosing the antenna assembly and feedthrough assembly. The antenna assembly including an inner conductor, a dielectric material, and an outer conductor arranged to form a coaxial structure.

Optionally, the dielectric material surrounds a perimeter of the inner conductor and the outer conductor surrounds a perimeter of the dielectric material. Optionally, the coaxial structure formed by the inner conductor, dielectric material and outer conductor is elongated and extends along a longitudinal axis. Wherein the inner conductor, the dielectric material, and outer conductor are formed concentrically about the longitudinal axis.

Optionally, the header body includes metallic components comprising at least one or a sensor electrode and receptacles configured to receive terminals on a lead. The coaxial structure avoiding RF coupling with the metallic components. Optionally the antenna assembly is formed with an ellipse shaped cross-section that includes a major portion and a minor portion, the major portion corresponding to the coaxial structure formed between the inner and outer conductors and dielectric material. The minor portion has a smaller diameter, relative to a diameter of the major portion, the minor portion including a ground conductor having a distal end fixed within an opening in the outer conductor, the inner and ground conductors extending in a common direction from a bottom surface of the antenna assembly.

Optionally, the inner conductor is elongated with a proximal end and a distal end, the inner conductor extending from a bottom surface of the antenna assembly by a predetermined length to at least partially tune the antenna assembly to a select communication frequency. Optionally, the antenna assembly includes a distal surface where the inner conductor, dielectric material and outer conductor terminate, the antenna assembly configured to generate RF fields between the inner and outer conductors at the distal surface in connection with RF communications.

Optionally, the device further comprising a pin receptacle mounted within the header body, the pin receptacle electrically coupled to the antenna assembly. The pin receptacle includes a pin retention cavity therein including a proximal end that is open to receive a feedthrough pin when the header body is mounted on the feedthrough assembly and the device housing. Optionally, the pin receptacle includes a spring mounted within the pin retention cavity, the spring configured to physically and electrically engage the feedthrough pin when inserted into the pin retention cavity.

In accordance with embodiments herein, an implantable medical device (IMD) is provided comprising a device housing having electronic components therein, and a feedthrough assembly joined to the device housing. The feedthrough assembly including a feedthrough pin coupled to the electronic components within the device housing. The feedthrough pin having a distal end extending from the feedthrough assembly. The device comprising an antenna assembly, a header body enclosing the antenna assembly, and a pin receptacle mounted within the header body. The pin receptacle including a pin retention cavity therein, the pin receptacle including a proximal end that is open to the pin retention cavity, the feedthrough pin configured to be inserted into the pin retention cavity when the header body is mounted on the feedthrough assembly and the device housing.

Optionally, the pin receptacle includes a spring mounted within the pin retention cavity. The spring is configured to physically and electrically engage the feedthrough pin when inserted into the pin retention cavity. Optionally, the pin receptacle includes a spring having a base securely affixed to an interior surface of the pin retention cavity. The spring includes spring arms projecting from the base into the pin retention cavity. The spring arms are configured to deflect when the feedthrough pin is inserted through the opening in the proximal end of the pin receptacle.

Optionally, the antenna assembly includes an inner conductor, a dielectric material, and an outer conductor arranged to form a coaxial structure, wherein the dielectric material surrounds a perimeter of the inner conductor and the outer conductor surrounds a perimeter of the dielectric material. Optionally, the dielectric material surrounds a perimeter of the inner conductor and an outer conductor surrounds a perimeter of the dielectric material.

Optionally, the antenna assembly is formed with an ellipse shaped cross-section that includes a major portion and a minor portion, the major portion corresponding to the coaxial structure formed between the inner and outer conductors and dielectric material. Optionally, the minor portion has a smaller diameter relative to the diameter of the major portion, the minor portion including a ground conductor having a distal end fixed within an opening in the outer conductor, the inner and ground conductors extending in a common direction from a bottom surface of the antenna assembly.

In accordance with embodiments herein, a method provides an implantable medical device (IMD). The method comprising assembly of a device housing having electronic components therein, joining a feedthrough assembly to the device housing, providing an antenna assembly including an inner conductor, a dielectric material, and an outer conductor arranged to form a coaxial structure. And assembling a header body that embeds the antenna assembly therein to the device housing and enclosing the antenna assembly and feedthrough assembly.

Optionally, the method further comprising inserting a feedthrough pin extending from the feedthrough assembly into a pin retention cavity of a pin receptacle electrically coupled to the antenna assembly when the header body is mounted on the feedthrough assembly and the device housing.

DETAILED DESCRIPTION

It will be readily understood that the components of the embodiments as generally described and illustrated in the figures herein, may be arranged and designed in a wide variety of different configurations in addition to the described example embodiments. Thus, the following more detailed description of the example embodiments, as represented in the figures, is not intended to limit the scope of the embodiments, as claimed, but is merely representative of example embodiments.

Reference throughout this specification to "one embodiment" or "an embodiment" (or the like) means that a particular feature, structure, or characteristic described in connection with the embodiment is included in at least one embodiment. Thus, appearances of the phrases "in one embodiment" or "in an embodiment" or the like in various places throughout this specification are not necessarily all referring to the same embodiment.

Figure 1A:
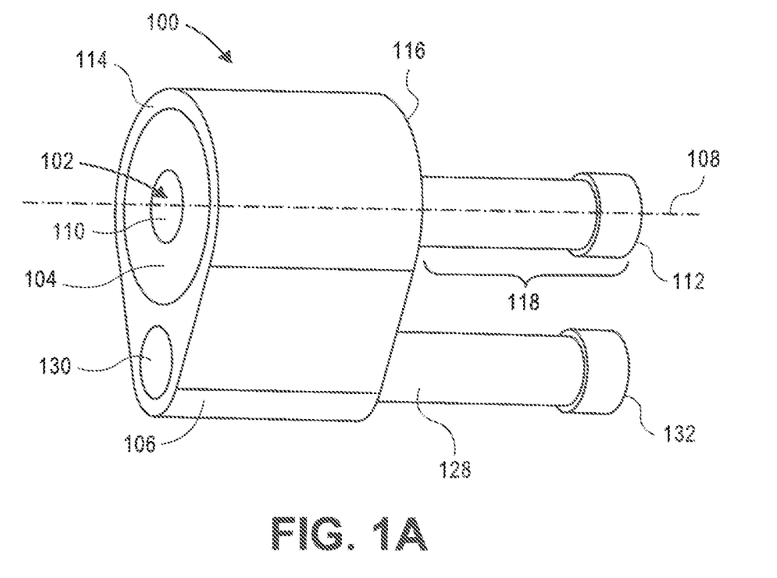
FIG. 1A illustrates a perspective view of an antenna assembly in accordance with embodiments herein.
Figure 1B:
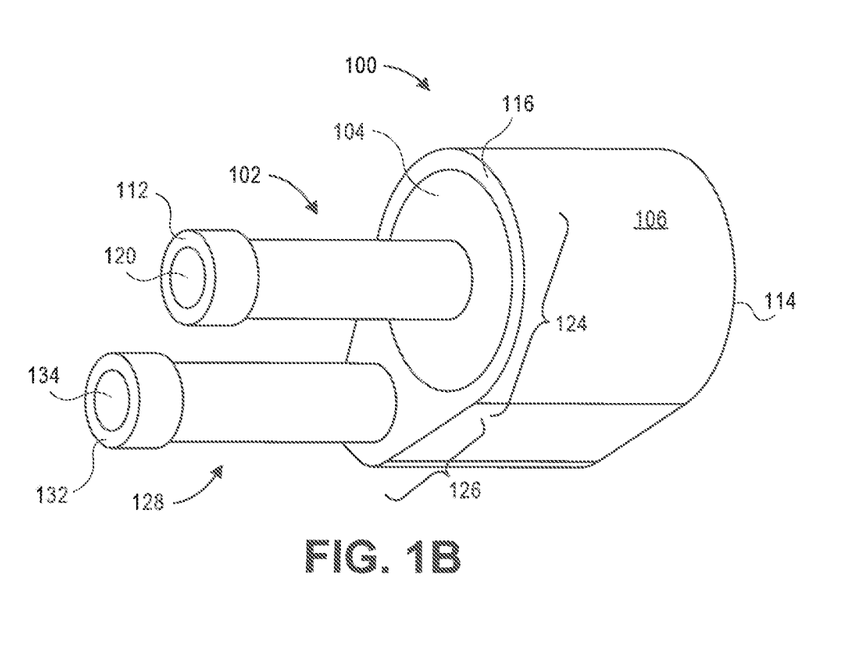
FIG. 1B illustrates an opposite perspective view of the antenna assembly of FIG. 1A.

FIGS. 1A and 1B illustrate opposite perspective end views of an antenna assembly formed in accordance with embodiments herein. With reference to FIG. 1A, the antenna assembly 100 includes an inner conductor 102, a dielectric material 104, and an outer conductor 106. The inner conductor 102, dielectric material 104 and outer conductor 106 are arranged relative to one another to form a coaxial structure. For example, the dielectric material 104 surrounds a perimeter of the inner conductor 102, while the outer conductor 106 surrounds a perimeter of the dielectric material 104. The antenna assembly 100 may utilize various coaxial structures. In the example of FIG. 1A, the coaxial structure is generally tubular, with the inner conductor, dielectric material and outer conductor elongated to extend along a longitudinal axis 108. The inner conductor 102, the dielectric material 104 and outer conductor 106 are formed concentrically about the longitudinal axis 108. Optionally, the antenna assembly 100 may be formed in alternative coaxial structures with alternative cross-sections, such as a rectangular cross-section, hexagonal cross-section, trapezoidal cross-section, oval cross-section, elliptical cross-section, triangular cross-section and the like.

The inner conductor 102 includes a distal end 110 and a proximal end 112. The distal end 110 terminates substantially flush with a distal surface 114 of the antenna assembly 100. Antenna assembly 100 also includes a bottom surface 116, from which the inner conductor 102 extends by predetermined distance 118.

FIG. 1B illustrates the antenna assembly 100 from an end opposite to the view illustrated in FIG. 1A. In FIG. 1B, the bottom surface 116 is more visible as well as the portion of the inner conductor 102 that extends from the dielectric material 104. The proximal end 112 of the inner conductor 102 includes an opening 120 that opens onto a pin retention cavity (described below in more detail in connection with FIG. 4) within the inner conductor 102. In the embodiment of FIGS. 1A and 1B, the inner conductor 102 is shaped to form a pin receptacle (described below in more detail in connection with FIG. 4). During the assembly, a feedthrough pin (extending from a feedthrough) is received through the opening 120 and extends into a pin retention cavity within the inner conductor 102.

Figure 4:
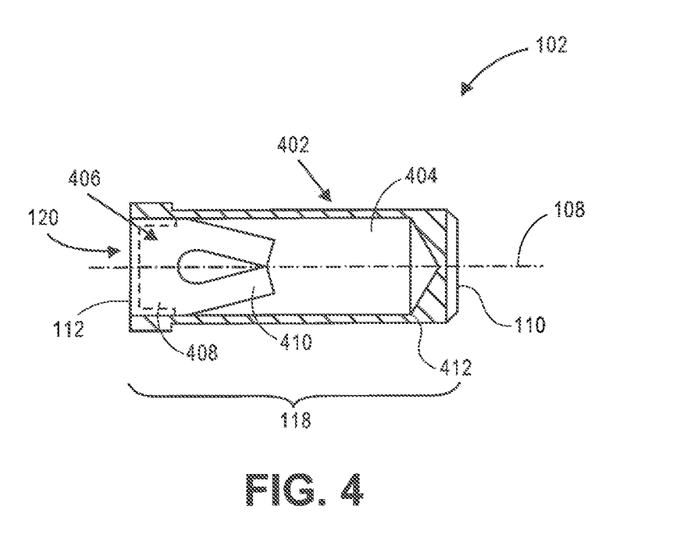
FIG. 4 illustrates a cross sectional view of a pin receptacle in accordance with embodiments herein.

The antenna assembly 100 is formed with an ellipse shaped cross-section that includes a major portion 124 and a minor portion 126. The major portion corresponds to the coaxial structure formed between the inner and outer conductors and dielectric material 102, 106 and 104. The minor portion 126 has a smaller diameter, relative to a diameter of the major portion 124. The minor portion 126 also includes a ground conductor 128 that extends into an opening within the outer conductor 106. The ground conductor 128 having a distal end 130 (FIG. 1A) fixed within an opening in the outer conductor 106. The distal end 130 terminates substantially flush with the distal surface 114 of the antenna assembly 100. The ground conductor 128 includes a proximal end 132. The proximal end 132 includes an opening 134 (FIG. 1B) that opens onto an internal pin retention cavity (FIG. 4). During the assembly, a ground feedthrough pin (extending from a feedthrough) is received through the opening 134 and extends into a pin retention cavity within the ground conductor 128.

The inner and ground conductors 102, 128 extend in a common direction from the bottom surface 116 of the antenna assembly 100. The ground conductor 128 extends from the bottom surface 116 by a predetermined distance 118 similar to a length of the inner conductor 102. For example, the ground conductor 128 may extend by the predetermined distance 118.

Figure 2:
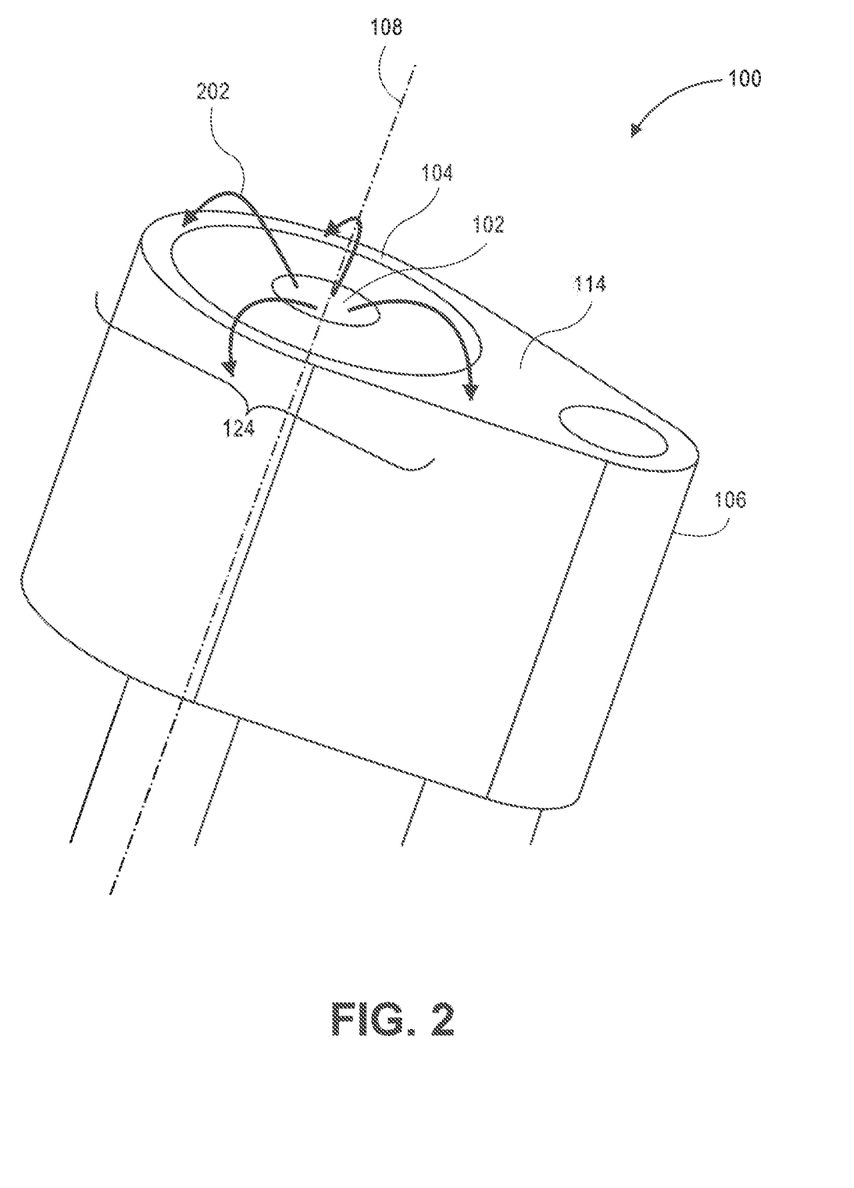
FIG. 2 illustrates a perspective view of RF fields radiating from the antenna assembly of FIG. 1A.

FIG. 2 illustrates a perspective view of RF fields 202 radiating from the antenna assembly 100 in accordance with embodiments herein. During RF communications, a voltage differential is created between the inner and outer conductors 102, 106. The voltage differential gives rise to RF fields 202 emitting from the distal surface 114 of the antenna assembly 100. The RF fields 202 radiate between the inner conductor 102 and the outer conductor 106. The RF fields 202 radiate uniformly or equally in all directions along the coaxial structure of the major portion 124 of the antenna assembly 100. For example, the RF fields 202 uniformly radiate between the inner and outer conductors 102, 106 about the longitudinal axis 108.

Figure 3:
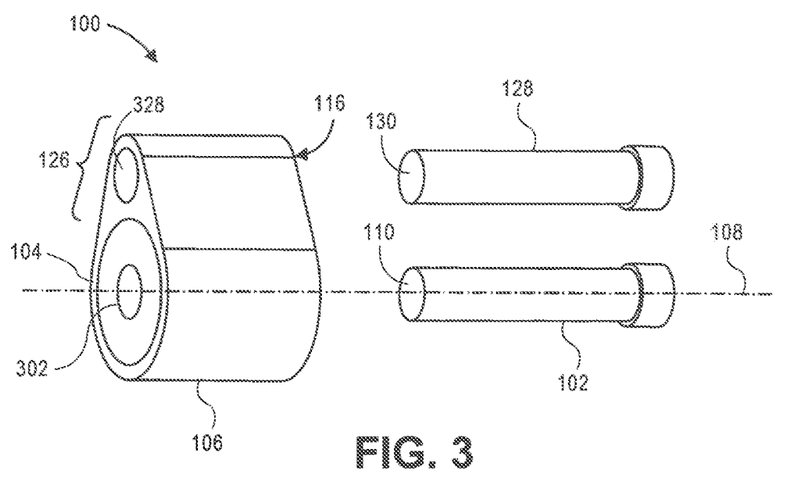
FIG. 3 illustrates an exploded view of the antenna assembly of FIG. 1A.

FIG. 3 illustrates an exploded view of the antenna assembly 100 in accordance with embodiments herein. The outer conductor 106 surrounds a perimeter of the dielectric material 104. The outer conductor 106 and the dielectric material 104 are elongated along the longitudinal axis 108. For example, the outer conductor 106 and the dielectric material 104 extend between the distal surface 114 and the bottom surface 116 of the antenna assembly 100. The dielectric material 104 has an inner passage 302. The inner passage 302 is hollow and extends between the distal surface 114 and the bottom surface 116 along the longitudinal axis 108. The inner passage 302 is shaped and sized to receive the inner conductor 102. For example, in the illustrated embodiment the inner passage 302 and the inner conductor 102 are generally tubular in shape. Optionally, the inner passage 302 and the inner conductor 102 may be formed in an alternative shape and size with alternative cross-sections. For example, the inner passage 302 and the inner conductor 102 may be formed of any alternative mating shapes.

The minor portion 126 (of FIG. 1B) of the antenna assembly 100 includes a ground passage 328. The ground passage 328 is hollow and extends between the distal surface 114 and the bottom surface 116 of the antenna assembly 100. The ground passage 328 is shaped and sized in order to receive the ground conductor 128. In the illustrated embodiment the ground passage 328 and the ground conductor 128 are generally tubular in shape. Optionally, the ground passage 328 and the ground conductor 128 may be formed in any other alternative shape and size with alternative cross-sections. For example, the ground passage 328 and the ground conductor 128 may be formed of any alternative mating shapes.

The antenna assembly 100 is formed by molding the inner conductor 102 within the inner passage 302 such that the distal end 110 of the inner conductor 102 is generally flush with the distal surface 114 of the antenna assembly 100. The ground conductor 126 is molded within the ground passage 328 such that the distal end 130 of the ground conductor 128 is generally flush with the distal surface 114 of the antenna assembly 100. The inner and ground conductors 102, 128 are held rigidly relative to the distal surface 114 of the antenna assembly 100 in a manner that eliminates axial movement and that eliminates rotation.

Optionally, the inner conductor 102 and the ground conductor 128 may be fixed within the inner passage 302 and the ground passage 328, respectively, by various methods. For example, the inner and ground conductors 102, 128 may be fixed within the inner and ground passages 302, 328 by casting, welding, mechanical fasteners, a tolerance press fit, or the like.

FIG. 4 illustrates a cross-sectional view of the inner conductor 102. The inner conductor 102 and the ground conductor 128 are configured with the same cross-sectional structure, therefore only the cross-section of the inner conductor 102 will be described in more detail. The inner conductor 102 is shaped to form a pin receptacle 402. The pin receptacle 402 is electrically coupled to the antenna assembly 100. The pin receptacle extends between the proximal end 112 and the distal end 110 of the inner conductor 102. For example, the pin receptacle extends the predetermined distance 118.

The pin receptacle 402 has a pin retention cavity 404 therein. The pin retention cavity 404 extends within the pin receptacle 402 along the longitudinal axis 108. The pin retention cavity 404 is open at the proximal end 112. The pin retention cavity 404 extends between the opening 120 at the proximal end 112 of the pin receptacle 402 and a closed end 412 proximate the distal end 110 of the pin receptacle 402.

The pin receptacle 402 includes a spring 406. The spring 406 is mounted within the phi reception cavity 404. The spring 406 is positioned within the phi retention cavity 404 proximate to the opening 120 at the proximal end 112.

The spring 406 has a spring base 408 and one or more spring arms 410. The spring base 408 is fixed within the pin retention cavity 404 near the opening 120. The one or more spring arms 410 project from the spring base 408 into the pin retention cavity 404. The spring arms 410 are biased towards the longitudinal axis 108. The spring arms 410 are configured to deflect when the spring 406 receives a feedthrough pin through the opening 120 of the pin receptacle 402. For example, the one or more spring arms 410 are configured to deflect away from the longitudinal axis 108 when a feedthrough pin is inserted into the pin retention cavity 404. The one or more spring arms 410 are configured to physically and electrically engage a feedthrough phi (described in more detail below with FIGS. 5A and 5B). In the illustrated embodiment of FIG. 4, the spring has two spring arms 410. Optionally, the spring 406 may have any number of spring arms 410. Alternatively, the pin receptacle 402 may have no spring arms.

Figure 5A:
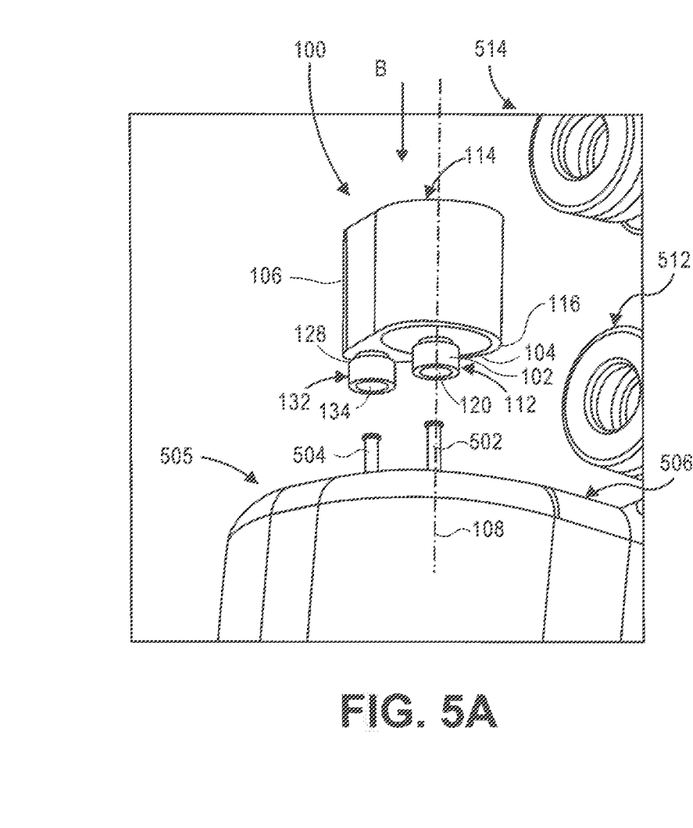
FIG. 5A illustrates a perspective view of an antenna assembly to be assembled with a device housing in accordance with embodiments herein.
Figure 5B:
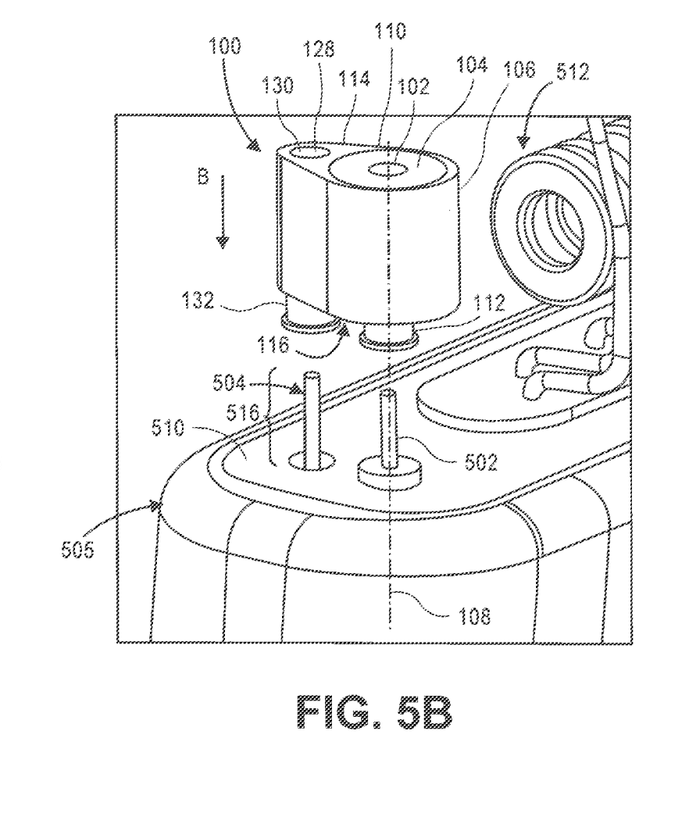
FIG. 5B illustrates a perspective view of an antenna assembly to be assembled with a device housing in accordance with embodiments herein.

FIGS. 5A and 5B illustrate a perspective view of the antenna assembly 100 to be assembled with a device housing 505 in accordance with embodiments herein. A feedthrough assembly is joined to the device housing. The device housing 505 has one or more of electrical components therein. For example, the one or more electrical components may represent transceiving circuitry such as one or more modems, transceivers, receivers, transmitters, or the like.

The device housing and a feedthrough assembly are part of an implantable medical device (IMD). The IMD may be configured to monitor electrical activity, and optionally to deliver therapy. For example, the IMD may record cardiac activity of a patient over time, may report such cardiac activity to an external device, and may perform various levels of sophisticated analysis of the cardiac activity and based thereon perform additional recording operations. Recognized embodiments can be implemented in any one or more IMDs of any one or more of neurostimulator devices, implantable leadless monitoring and/or therapy devices, or alternative implantable medical devices. For example, the IMD may represent a cardiac monitoring device, pacemaker, cardioverters, cardiac rhythm management devices, defibrillators, neurostimulators, leadless monitoring devices, and the like. FIGS. 5A and 5B may represent a device housing of a neurostimulator device. See for example U.S. Pat. No. 9,333,351 "Neurostimulation Method And System To Treat Apnea" and U.S. Pat. No. 9,044,610 "System And Methods For Providing A Distributed Virtual Stimulation Cathode For Use With An Implantable Neurostimulation System", which are hereby incorporated by reference. Additionally or alternatively, FIGS. 5A and 5B may represent a device housing of a leadless IMD. See for example U.S. Pat. No. 9,216,285 "Leadless Implantable Medical Device Having Removable And Axed Components" and U.S. Pat. No. 8,831,747 "Leadless Neurostimulation Device And Method Including The Same", which are hereby incorporated by reference. Additionally or alternatively, FIGS. 5A and 5B may represent a device housing of an alternative IMD. See for example U.S. Pat. No. 8,391,980 "Method And System For Identifying A Potential Lead Failure In An Implantable Medical Device" and U.S. Pat. No. 9,232,485 "System And Method For Selectively Communicating With An Implantable Medical Device", which are hereby incorporated by reference.

In the illustrated embodiments of FIGS. 5A and 5B, the antenna assembly 100 is separate from the device housing 505. The antenna assembly 100 is embedded in a header body (not shown, described in more detail below with FIGS. 8 and 9). The opening 120 of the inner conductor 102 is axially aligned with a feedthrough pin 502 extending through and in a direction generally away from a proximate surface 510 of the device housing 505. For example, the feedthrough pin 502 may extend by a predetermined distance 516. Additionally, the opening 134 of the ground conductor 128 is axially aligned with a ground feedthrough pin 504 extending through and in a direction generally away from the proximate surface 510. For example, the ground feedthrough pin 504 may extend by the predetermined distance 516.

The inner conductor 102 and the ground conductor 128 are positioned in order to receive the feedthrough pin 502 and the ground feedthrough pin 504, respectively, into the pin receptacles of the inner and ground conductors 102, 128. For example, the inner conductor 102 and the ground conductor 128 receive the feedthrough pin 502 and the ground feedthrough pin 504 into the openings 120, 134, respectively, when the antenna assembly is loaded in a direction B along the longitudinal axis 108.

The one or more springs arms 410 retain the antenna assembly 100 on the feedthrough pin 602 and ground feedthrough pin 504 of the device housing 505. The spring arms 410 of the inner conductor 102 electrically and physically engages the feedthrough pin 502 when the feedthrough pin 502 is inserted into the pin retention cavity. For example, the antenna assembly 100 is operably connected with the electrical components of the device housing 505 when the spring arms 410 of the pin retention cavity of the inner conductor 102 electrically and physically engage the feedthrough pin 502. Additionally, the spring arms 410 of the ground conductor 128 electrically and physically engage the ground feedthrough pin 504 when the ground feedthrough pin 504 is inserted into the pin retention cavity. The ground conductor 128 grounds the antenna assembly 100 to the device housing 505 when the spring arms 410 electrically and physically engage the ground feedthrough pin 504.

The antenna assembly 100 is joined to the device housing 505 by the feedthrough pin and ground feedthrough pin 502, 504 received within the inner conductor and the ground conductor 102, 128. For example, the spring arms 410 (FIG. 4) of the pin receptacle of the inner conductor 102 and the ground conductor 128 maintain a linear position of the antenna assembly 100 assembled onto the feedthrough pin 502 and ground feedthrough pin 504. Optionally, in an alternative embodiment, the inner conductor and the ground conductor may be devoid of a spring. In an alternative embodiment, an inner conductor and a ground conductor may be joined to a feedthrough pin and a ground feedthrough pin by alternative methods. For example, the alternative inner and ground conductors may be joined to the feedthrough and ground feedthrough pins by soldering, welding, crimping, alternative mechanical fastening or the like.

FIGS. 5A and 58 include one or more of metallic components 512, 514. The metallic components 512, 514 may comprise one or more of a sensor electrode, connector blocks or receptacle configured to receive terminals on a proximal end of one or more leads. The metallic components 512, 514 are operably connected with the electrical components within the device housing 505.

Figure 6:
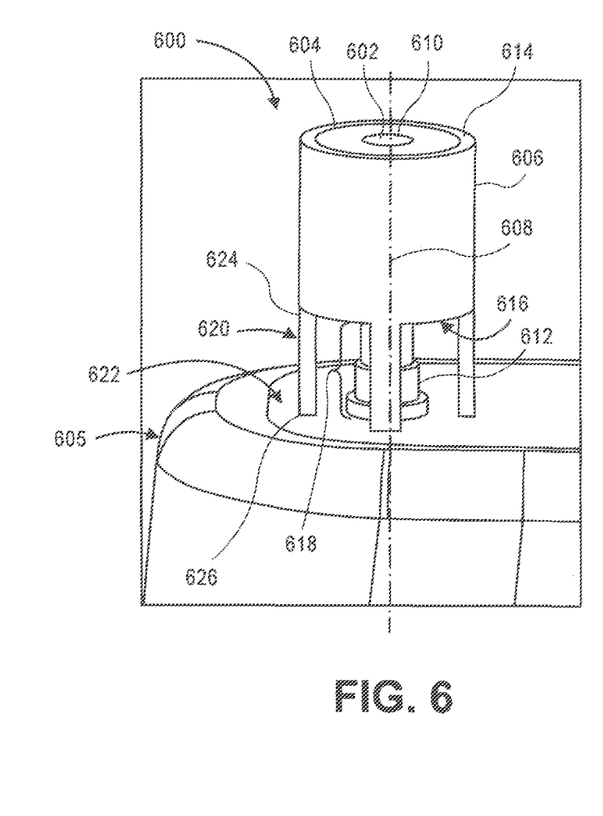
FIG. 6 illustrates a perspective view of an antenna assembly joined to a device housing in accordance with embodiments herein.

FIG. 6 illustrates an alternative embodiment of an antenna assembly assembled to a device housing. An antenna assembly 600 has an inner conductor 602, a dielectric material 604, and an outer conductor 606 (corresponding to the inner conductor, dielectric material and outer conductor 102, 104, 106 of FIG. 1). The inner conductor 602, dielectric material 604 and outer conductor 606 are arranged concentric relative to one another to form a coaxial structure. The antenna assembly 600 may utilize various coaxial structures. In the example of FIG. 6, the coaxial structure is generally tubular, with the inner conductor, dielectric material and outer conductor elongated to extend along a longitudinal axis 608. The inner conductor 602, the dielectric material 604 and the outer conductor 606 are formed concentrically about the longitudinal axis 608.

The inner conductor 602 includes a distal end 610 and a proximal end 612. The distal end 610 terminates substantially flush with a distal surface 614 of the antenna assembly 600. Antenna assembly 600 also includes a bottom surface 616, from which the inner conductor 602 extends by a predetermined distance 618.

In the embodiment of FIG. 6, the inner conductor 602 is shaped to form a pin receptacle (e.g., corresponding to the pin receptacle 402 of FIG. 4). The proximal end 612 of the inner conductor 602 includes an opening that opens onto a pin retention cavity (e.g., corresponding to the pin retention cavity 404 of FIG. 4) within the inner conductor 602. During the assembly, a feedthrough pin (e.g., corresponding to the feedthrough pin 502 of FIG. 5A) extending from a device housing 605 is received into the opening and extends into the pin retention cavity within the inner conductor 602. One or more spring arms (e.g., corresponding to the spring arms 410 of FIG. 4) physically and electrically engage the feedthrough pin when the feedthrough pin is inserted into the pin retention cavity of the inner conductor 602.

The outer conductor 606 has one or more ground arms 620 evenly distributed about a perimeter of the outer conductor 606. The ground arms 620 extend from the bottom surface 616 of the antenna assembly 600 in a direction generally away from the antenna assembly 600. The ground arms 620 have a distal end 624 positioned near the bottom surface 616 of the antenna assembly. The ground arms 620 have a proximal end 626 located remote from the bottom surface 616. In the illustrated embodiment, three ground arms 620 extend from the bottom surface 616 of the antenna assembly 600. Optionally, the antenna assembly may have any number of ground arms 620. For example, the antenna assembly may comprise one or two ground arms. Additionally or alternatively, the antenna assembly may have more than three ground arms.

In the illustrated embodiment of FIG. 6, the ground arms 620 have a rectangular cross-section and are elongated along the longitudinal axis 608. Optionally, the ground arms 620 may have any alternative cross-sectional shape. Additionally or alternatively, the ground arms 620 may have a common cross-section shape and/or size, or unique cross-section shapes and/or sizes.

The inner conductor 602 and the ground arms 620 extend in a common direction from the bottom surface 616 of the antenna assembly 600. The ground arms 620 extend from the bottom surface 616 by a length similar to or longer than the length of the inner conductor 602. For example, the ground arms 620 may extend by the predetermined distance 618.

The pin receptacle of the inner conductor 602 receives the feedthrough phi when the antenna assembly 600 is joined to the device housing 605. The one or more spring arms of the pin receptacle electrically and physically engage the feedthrough pin when the feedthrough pin is inserted into the pin retention cavity.

Figure 7:
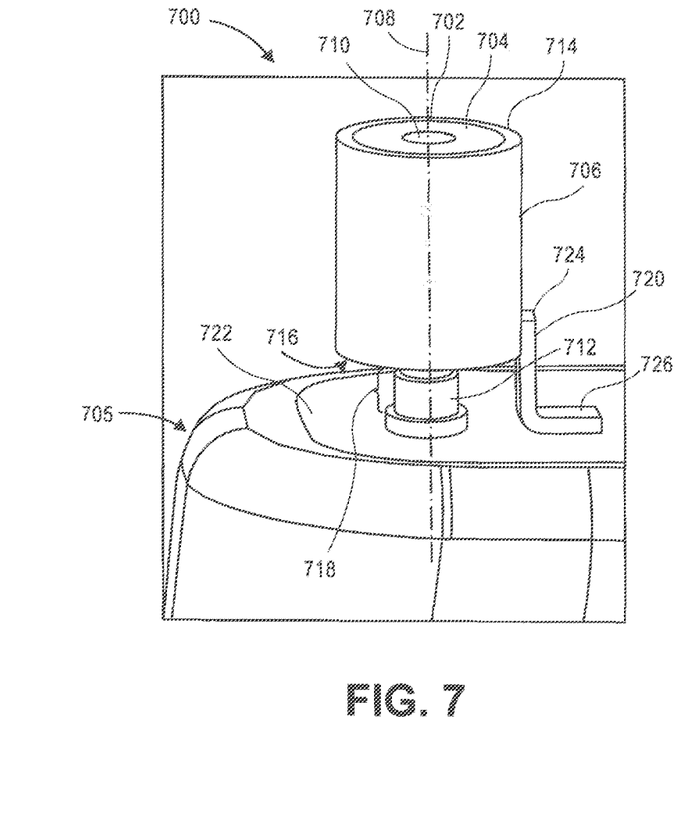
FIG. 7 illustrates a perspective view of an antenna assembly joined to a device housing in accordance with embodiments herein.

FIG. 7 illustrates an alternative embodiment of an antenna assembly assembled to a device housing. An antenna assembly 700 has an inner conductor 702, a dielectric material 704, and an outer conductor 706 (corresponding to the inner conductor, dielectric material, and outer conductor 102, 104, 106 of FIG. 1). The inner conductor 702, dielectric material 704 and outer conductor 706 are arranged relative to one another to form a coaxial structure. The antenna assembly 700 may utilize various coaxial structures. The coaxial structure includes a generally tubular cross-section, with the inner conductor, dielectric material and outer conductor elongated to extend along a longitudinal axis 708. The inner conductor 702, the dielectric material 704 and the outer conductor 706 are formed concentrically about the longitudinal axis 708.

The inner conductor 702 includes a distal end 710 and a proximal end 712. The distal end 710 terminates substantially flush with a distal surface 714 of the antenna assembly 700. Antenna assembly 700 also includes a bottom surface 716, from which the inner conductor 702 extends by a predetermined distance 718.

The proximal end 712 of the inner conductor 702 includes an opening that opens onto a pin retention cavity (e.g., corresponding to the pin retention cavity 404 of FIG. 4) within the pin receptacle of the inner conductor 702.

The antenna assembly 700 includes a grounding bar 720 that has a distal end 724 and a proximal end 726. The distal end 724 is physically and electrically engaged with a perimeter of the outer conductor 706. The proximal end 726 is physically and electrically engaged with a proximate surface 722 of the device housing 705. The grounding bar 720 has an L-shape profile with a plane of the distal end 724 generally perpendicular with a plane of the proximal end 726.

Optionally, the grounding bar 720 may utilize alternative positions, shapes and/or sizes in order to physically and electrically engage the outer conductor 706 with the device housing 705.

Figure 8:
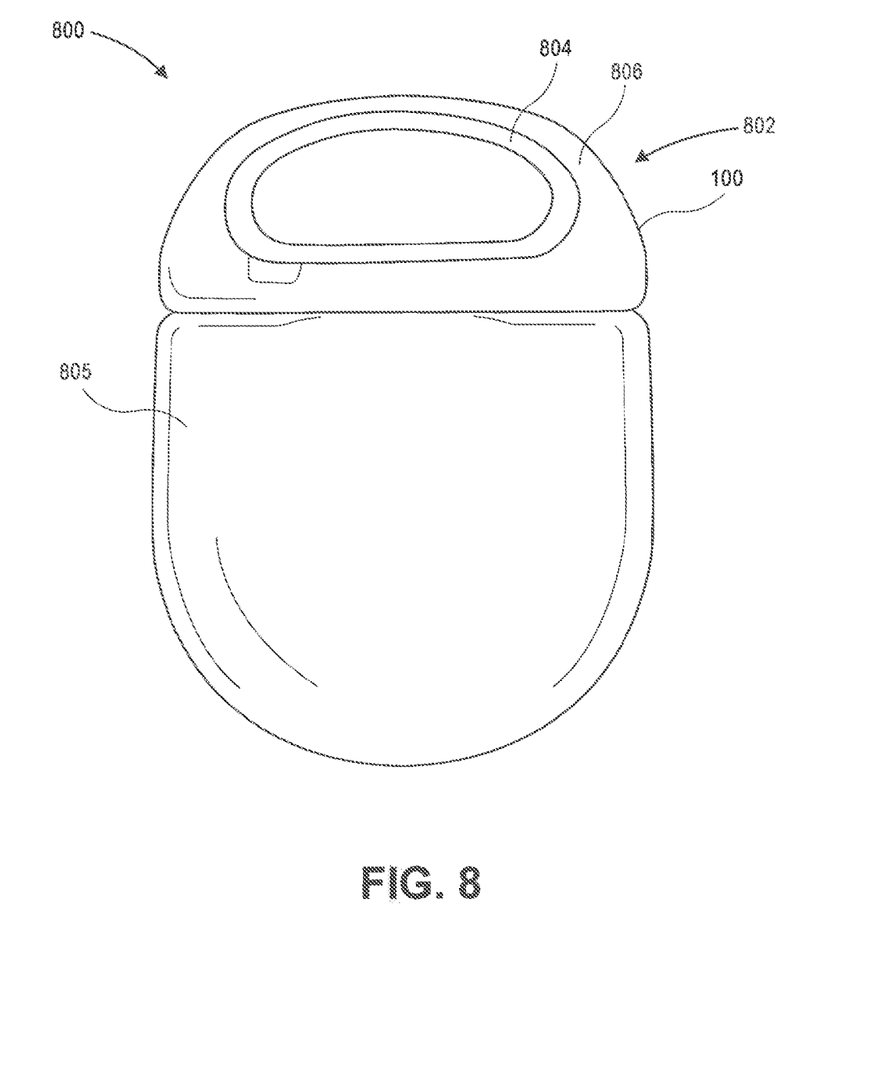
FIG. 8 illustrates a perspective view of an implantable medical device in accordance with embodiments herein.
Figure 9:
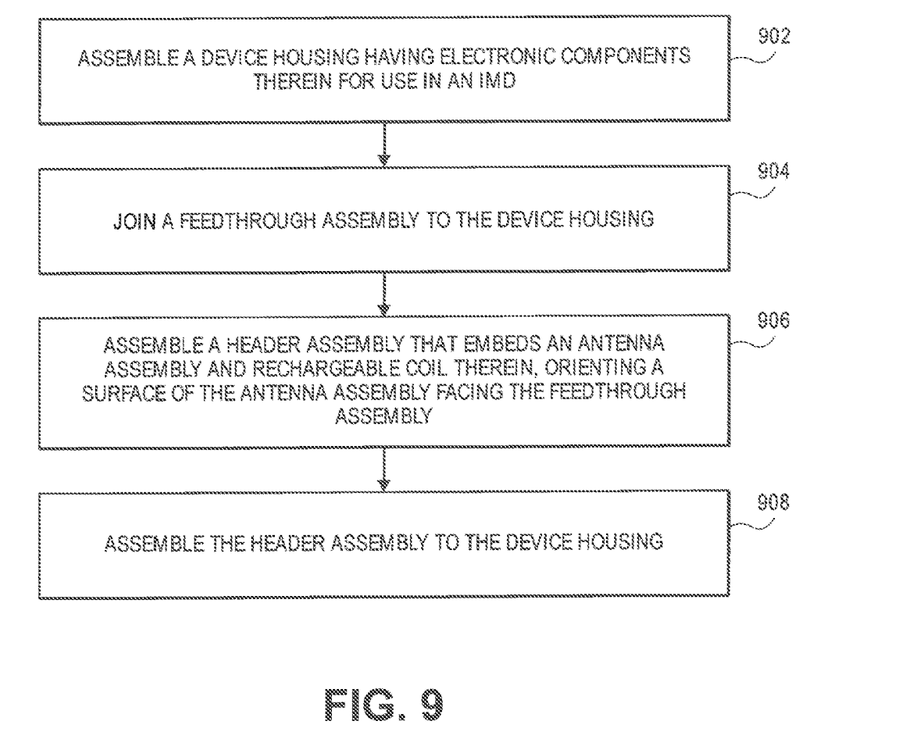
FIG. 9 illustrates a method for providing an implantable medical device in accordance with embodiments herein.

FIG. 8 illustrates a perspective view of an implantable medical device (IMD) in accordance with an embodiment herein. FIG. 9 illustrates a method for providing an IMD in accordance with an embodiment herein. The operations of FIG. 9 will be described in connection with FIG. 8.

An IMD 800 has a device housing 805. At 902 of FIG. 9, the process includes assembling the device housing 805 having electronic components therein. Examples of the various electronic components are described herein. The electronic components may include a memory, sensing circuitry to sense cardiac signals of interest, one or more processors to perform monitoring operations, transceiver circuitry to communicate with external devices and other components of the like. The memory, processors, and other electronic components are assembled within the device housing 805 formed of a biocompatible material.

At 904, the process includes joining a feedthrough assembly to the device housing 805. The housing 805 includes a feedthrough opening at one end The feedthrough assembly is welded to the feedthrough opening, thereby hermetically sealing the interior of the device housing 805.

The IMD 800 has a header assembly 802. At 906, the header assembly 802 is assembled by embedding the antenna assembly 100, a rechargeable coil 804, and one or more metallic components (e.g., sensor leads, receptacles, connector blocks or the like) within a header body 806. The rechargeable coil 804 extends about a majority of the header body 806. For example, the rechargeable coil 804 includes one or more windings that extend along a length of the header assembly 802. A portion of the windings extend along bottom, end, and distal edges of the header assembly 802. The antenna assembly 100 is oriented with the bottom surface 116 facing towards the feedthrough pin 502 and the ground feedthrough pin 504 extending from the feedthrough assembly of the device housing 805.

At 908, the header assembly 802 is assembled to the device housing 805. The process of assembly includes the antenna assembly 100 operably connecting with the electronic components within the device housing 805. For example, the one or more spring arms of the inner conductor and ground conductor 102, 128 of the antenna assembly 100 are physically and electrically engaged with the feedthrough pin 502 and ground feedthrough pin 504 (FIG. 5A). Additionally, the rechargeable coil 804 is operably connected with the electronic components within the device housing 805. The header assembly 802 is welded to the device housing 805, thereby hermetically sealing the IMD 800. For example, the header assembly 802 assembled to the device housing 805 encloses the antenna assembly 100 and the feedthrough assembly.

Figure 10A:
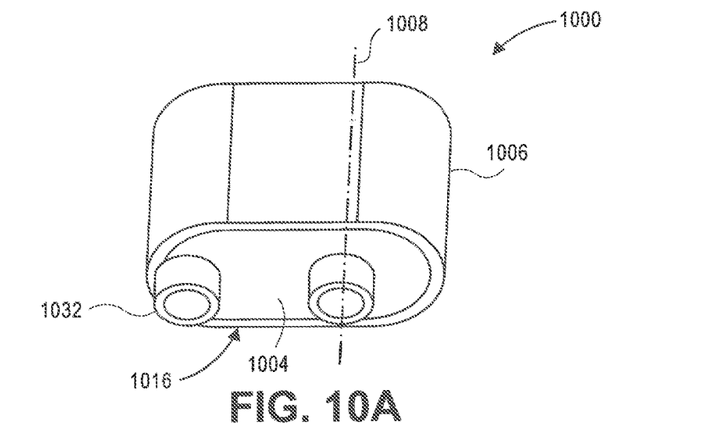
FIG. 10A illustrates a perspective view of an antenna assembly hi accordance with embodiments herein.
Figure 10B:
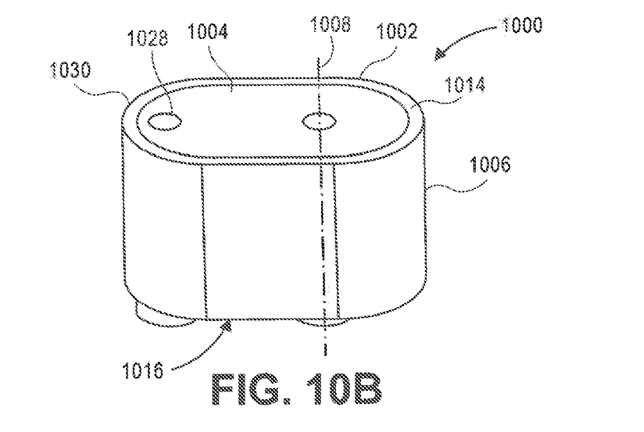
FIG. 10B illustrates an opposite perspective view of the antenna assembly of FIG. 10A.

FIGS. 10A and 10B illustrates an alternative cross-section of an antenna assembly 1000. The antenna assembly 1000 includes an inner conductor 1002, a dielectric material 1004, and an outer conductor 1006. The outer conductor 1006 and the dielectric material 1004 have a generally uniform oval cross-section shape, and the inner conductor 1002 has a circular cross-section. The dielectric material 1004 surrounds a perimeter of the inner conductor 1002, while the outer conductor 1006 surrounds a perimeter of the dielectric material 1004. The inner conductor 1002, dielectric material 1004 and outer conductor 1006 are arranged relative to one another to form an eccentric structure. The inner conductor 1002, dielectric material 1004 and outer conductor 1006 are elongated to extend along a longitudinal axis 1008.

Figure 10C:
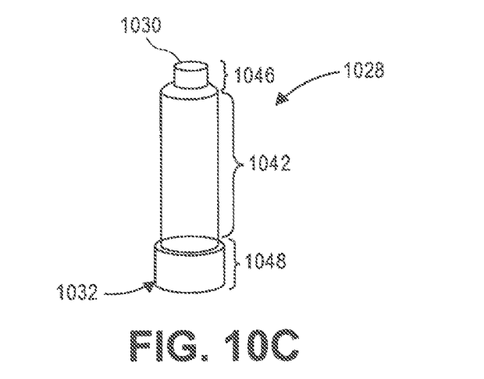
FIG. 10C illustrates a perspective view of a ground conductor in accordance with embodiments herein.

FIG. 10C illustrates a perspective view of a ground conductor 1028 in accordance with an embodiment herein. The ground conductor 1028 and inner conductor 1002 are generally the same shape and size. Only the ground conductor 1028 will be described in more detail.

The ground conductor 1028 has a circular cross-section and is generally tubular along the longitudinal axis 1008 between a distal end 1030 and a proximal end 1032. The ground conductor 1028 has a header portion 1046 positioned proximate the distal end 1030 and a bottom portion 1048 positioned proximate the proximal end 1032. A body portion 1042 extends between the header portion 1046 and the bottom portion 1048. The header portion 1046, the body portion 1042 and the bottom portion 1048 are generally concentric. The body portion 1042 has a length that is longer relative to a length of the header portion 1046 and a length of the bottom portion 1048.

The ground conductor 1028 is tapered between the distal and proximal ends 1030, 1032. For example, a diameter of the header portion 1046 is smaller relative to a diameter of the body portion 1042, and the diameter of the body portion 1042 is smaller relative to a diameter of the bottom portion 1048.

Returning to FIGS. 10A and 10B, the ground conductor 1028 is molded within an opening of the antenna assembly 1000. The distal end 1030 terminates substantially flush with the distal surface 1014 of the antenna assembly 1000.

The dielectric material 1004 surrounds a perimeter of the header portion 1046 at the distal surface 1014. The bottom portion 1048 of the ground conductor 1028 extends from a bottom surface 1016. A perimeter of the body portion 1042 is surrounded partially by the dielectric material 1004 and partially by the outer conductor 1006. The proximal end 1032 touches the outer conductor 1006 at the bottom surface 1016 of the antenna assembly 1000. For example, the ground conductor 1028 is electrically and physically engaged with the outer conductor 1006.

The inner conductor 1002 and the ground conductor 1028 are positioned in order to receive a feedthrough pin and a ground feedthrough pin (e.g., corresponding to the feedthrough pin 502 and the ground feedthrough pin 504 of FIG. 5A).

Figure 11:
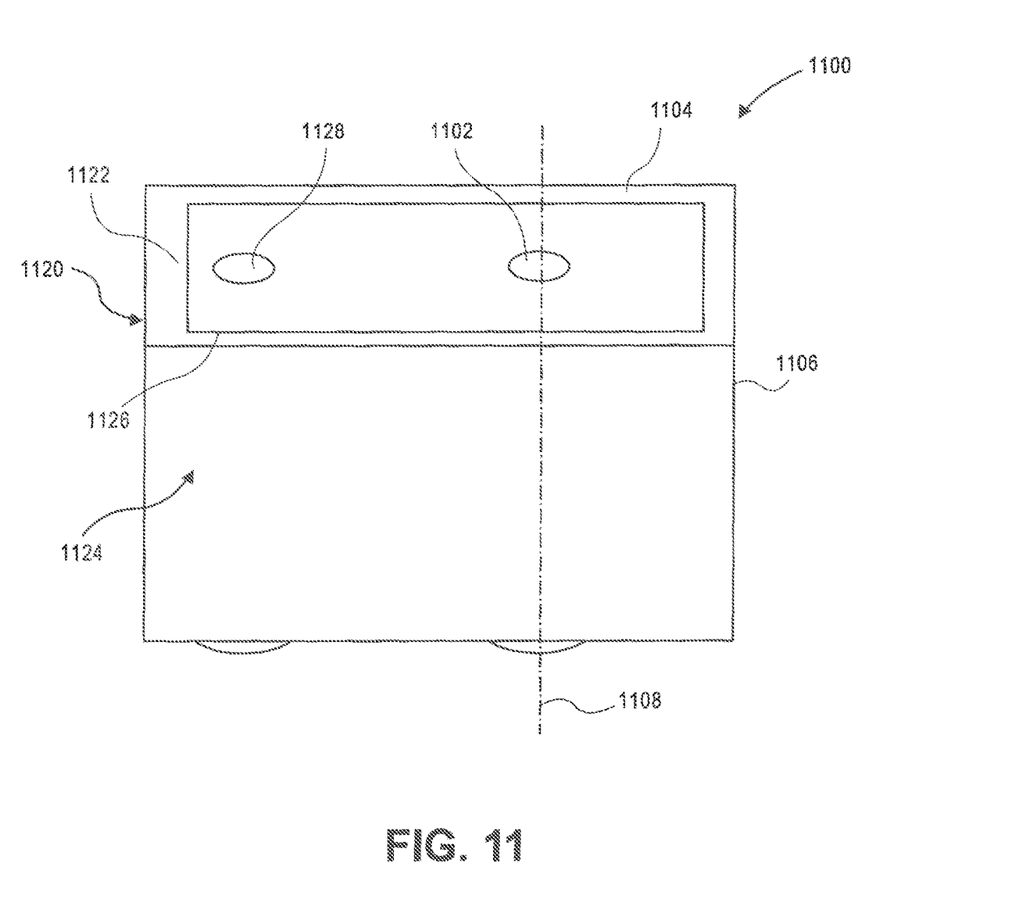
FIG. 11 illustrates a perspective view of an antenna assembly in accordance with embodiments herein.

FIG. 11 illustrates an alternative cross-section of an antenna assembly 1100. The antenna assembly 1100 corresponds to the antenna assembly 1000 of FIGS. 10A and 10B. An outer conductor 1106 and a dielectric material 1104 have a concentric rectangular cross-section with parallel side walls 1120, 1122, and parallel end walls 1124, 1126. An inner conductor 1102 has a circular cross-section. The inner conductor 1102, dielectric material 1104, and outer conductor 1106 extend along a longitudinal axis 1108.

A ground conductor 1128 (corresponding to the ground conductor 1028 of FIG. 10C) is assembled with the antenna assembly 1100. A perimeter of a body portion (e.g., body portion 1042 of FIG. 10C) is surrounded partially by the dielectric material 1104 and partially by the outer conductor 1106. The ground conductor 1128 is electrically and physically engaged with the outer conductor 1106. The inner conductor 1102 and the ground conductor 1128 are positioned in order to receive a feedthrough pin and a ground feedthrough pin (e.g., corresponding to the feedthrough pin 502 and the ground feedthrough pin 504 of FIG. 5A).

FIGS. 10A, 10B and 11 illustrate an antenna assembly having an outer conductor and a dielectric material with a common, concentric cross-section. Optionally, the outer conductor may have cross-section that is unique relative to the dielectric material.

The various methods as illustrated in the FIGS. and described herein represent exemplary embodiments of methods. The methods may be implemented in software, hardware, or a combination thereof. In various of the methods, the order of the steps may be changed, and various elements may be added, reordered, combined, omitted, modified, etc. Various of the steps may be performed automatically (e.g., without being directly prompted by user input) and/or programmatically (e.g., according to program instructions).

Various modifications and changes may be made as would be obvious to a person skilled in the art having the benefit of this disclosure. It is intended to embrace all such modifications and changes and, accordingly, the above description is to be regarded in an illustrative rather than a restrictive sense.

The specification and drawings are, accordingly, to be regarded in an illustrative rather than a restrictive sense. It will, however, be evident that various modifications and changes may be made thereunto without departing from the broader spirit and scope of the invention as set forth in the claims.

Other variations are within the spirit of the present disclosure. Thus, while the disclosed techniques are susceptible to various modifications and alternative constructions, certain illustrated embodiments thereof are shown in the drawings and have been described above in detail it should be understood, however, that there is no intention to limit the invention to the specific form or forms disclosed, but on the contrary, the intention is to cover all modifications, alternative constructions and equivalents falling within the spirit and scope of the invention, as defined in the appended claims.

The use of the terms "a" and "an" and "the" and similar referents in the context of describing the disclosed embodiments (especially in the context of the following claims) are to be construed to cover both the singular and the plural, unless otherwise indicated herein or clearly contradicted by context. The terms "comprising," "having," "including" and "containing" are to be construed as open-ended terms (i.e., meaning "including, but not limited to,") unless otherwise noted. The term "connected," when unmodified and referring to physical connections, is to be construed as partly or wholly contained within, attached to or joined together, even if there is something intervening. Recitation of ranges of values herein are merely intended to serve as a shorthand method of referring individually to each separate value falling within the range, unless otherwise indicated herein and each separate value is incorporated into the specification as if it were individually recited herein. The use of the term "set" (e.g., "a set of items") or "subset" unless otherwise noted or contradicted by context, is to be construed as a nonempty collection comprising one or more members. Further, unless otherwise noted or contradicted by context, the term "subset" of a corresponding set does not necessarily denote a proper subset of the corresponding set, but the subset and the corresponding set may be equal.

All references, including publications, patent applications and patents, cited herein are hereby incorporated by reference to the same extent as if each reference were individually and specifically indicated to be incorporated by reference and were set forth in its entirety herein.

It is to be understood that the subject matter described herein is not limited in its application to the details of construction and the arrangement of components set forth in the description herein or illustrated in the drawings hereof. The subject matter described herein is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the invention without departing from its scope. While the dimensions, types of materials and coatings described herein are intended to define the parameters of the invention, they are by no means limiting and are exemplary embodiments. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein," Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 § 112(f), unless and until such claim limitations expressly use the phrase "means for" followed by a statement of function void of further structure.

What is claimed is:

1. An implantable medical device, comprising:
    a device housing having electronic components therein;
    a feedthrough assembly joined to the device housing;
    an antenna assembly; and
    a header body mounted to the device housing and enclosing the antenna assembly and feedthrough assembly,
    the antenna assembly including an inner conductor, an outer conductor and a dielectric material disposed between the inner conductor and the outer conductor, wherein the inner conductor, the dielectric material and the outer conductor are concentrically arranged relative to one another about a longitudinal axis to form a tubular coaxial structure.

2. The device of claim 1, wherein the dielectric material surrounds a perimeter of the inner conductor and the outer conductor surrounds a perimeter of the dielectric material.

3. The device of claim 1, wherein the header body includes metallic components comprising at least one of a sensor electrode and receptacles configured to receive terminals on a lead, the tubular coaxial structure avoiding RF coupling with the metallic components.

4. The device of claim 1, wherein the antenna assembly is formed with an ellipse shaped cross-section that includes a major portion and a minor portion, the major portion corresponding to the tubular coaxial structure formed of the inner and outer conductors and dielectric material.

5. The device of claim 4, wherein the minor portion has a smaller diameter, relative to a diameter of the major portion, the minor portion including a ground conductor having a distal end fixed within an opening in the outer conductor, the inner and ground conductors extending in a common direction from a bottom surface of the antenna assembly.

6. The device of claim 1, wherein the inner conductor is elongated with a proximal end and a distal end, the inner conductor extending from a bottom surface of the antenna assembly by a predetermined length to at least partially tune the antenna assembly to a select communication frequency.

7. The device of claim 1, wherein the antenna assembly includes a distal surface where the inner conductor, dielectric material and outer conductor terminate, the antenna assembly configured to generate RF fields between the inner and outer conductors at the distal surface in connection with RF communications.

8. The device of claim 1, further comprising a pin receptacle mounted within the header body, the pin receptacle electrically coupled to the antenna assembly.

9. The device of claim 8, wherein the pin receptacle includes a spring mounted within the pin retention cavity, the spring configured to physically and electrically engage the feedthrough pin when inserted into the pin retention cavity.

10. The device of claim 1, further comprising a pin receptacle, wherein the pin receptacle includes a pin retention cavity therein including a proximal end that is open to receive a feedthrough pin when the header body is mounted on the feedthrough assembly and the device housing.

11. An implantable medical device, comprising:
    a device housing having electronic components therein;

a feedthrough assembly joined to the device housing, the feedthrough assembly including a feedthrough pin coupled to the electronic components within the device housing, the feedthrough pin having a distal end extending from the feedthrough assembly;

an antenna assembly;

a header body enclosing the antenna assembly; and a pin receptacle mounted within the header body, the pin receptacle electrically coupled to the antenna assembly, the pin receptacle including a pin retention cavity therein, the pin receptacle including a proximal end that is open to the pin retention cavity, the feedthrough pin configured to be inserted into the pin retention cavity when the header body is mounted on the feedthrough assembly and the device housing, the antenna assembly including an inner conductor, an outer conductor and a dielectric material disposed between the inner conductor and the outer conductor, wherein the inner conductor, the dielectric material and the outer conductor are concentrically arranged relative to one another to form a tubular coaxial structure having a longitudinal axis.

12. The device of claim 11, wherein the pin receptacle includes a spring mounted within the pin retention cavity, the spring configured to physically and electrically engage the feedthrough pin when inserted into the pin retention cavity.

13. The device of claim 11, wherein the pin receptacle includes a spring having a base securely affixed to an interior surface of the pin retention cavity, the spring including spring arms projecting from the base into the pin retention cavity, the spring arms configured to deflect when the feedthrough pin is inserted through the opening in the proximal end of the pin receptacle.

14. The device of claim 11, wherein the dielectric material surrounds a perimeter of the inner conductor and the outer conductor surrounds a perimeter of the dielectric material.

15. The device of claim 11, wherein the antenna assembly is formed with an ellipse shaped cross-section that includes a major portion and a minor portion, the major portion corresponding to the coaxial structure formed of the inner and outer conductors and dielectric material.

16. The device of claim 15, wherein the minor portion has a smaller diameter relative to the diameter of the major portion, the minor portion including a ground conductor having a distal end fixed within an opening in the outer conductor, the inner and ground conductors extending in a common direction from a bottom surface of the antenna assembly.

17. A method for providing an implantable medical device, comprising:

assembling a device housing having electronic components therein;

joining a feedthrough assembly to the device housing;

providing an antenna assembly including an inner conductor, an outer conductor and a dielectric material disposed between the inner conductor and the outer conductor, wherein the inner conductor, the outer conductor and the dielectric material are concentrically arranged relative to one another about a longitudinal axis to form a tubular coaxial structure; and assembling a header body that embeds the antenna assembly therein to the device housing and enclosing the antenna assembly and feedthrough assembly.

18. The method of claim 17, further comprising inserting a feedthrough pin extending from the feedthrough assembly into a pin retention cavity of a pin receptacle electrically coupled to the antenna assembly when the header body is mounted on the feedthrough assembly and the device housing.

* * * * *